United States Patent
Terranova et al.

(10) Patent No.: US 6,660,046 B1
(45) Date of Patent: Dec. 9, 2003

(54) CATIONIC OXIDATION BASES, THEIR USE OF DYEING KERATIN FIBRES, DYEING COMPOSITIONS AND DYEING METHODS

(75) Inventors: Eric Terranova, Bois Colombes (FR); Alain Lagrange, Coupvray (FR)

(73) Assignee: L'Oreal S.A., Paris (FR)

( * ) Notice: Subject to any disclaimer, the term of this patent is extended or adjusted under 35 U.S.C. 154(b) by 0 days.

(21) Appl. No.: 09/889,502

(22) PCT Filed: Jan. 14, 2000

(86) PCT No.: PCT/FR00/00074

§ 371 (c)(1),
(2), (4) Date: Aug. 30, 2001

(87) PCT Pub. No.: WO00/43367

PCT Pub. Date: Jul. 27, 2000

(30) Foreign Application Priority Data

Jan. 19, 1999 (FR) .............................................. 99 00505

(51) Int. Cl.$^7$ ................................................. A61K 7/13
(52) U.S. Cl. ....................... 8/405; 8/406; 8/409; 8/411; 8/412; 8/423; 8/572; 8/573; 548/371.4; 548/371.7; 548/372.5
(58) Field of Search ........................... 8/405, 406, 409, 8/411, 412, 423, 572, 573; 548/371.4, 371.7, 372.5

(56) References Cited

U.S. PATENT DOCUMENTS

| | | | |
|---|---|---|---|
| 4,003,699 A | 1/1977 | Rose et al. ................ | 8/10.2 |
| 4,823,985 A | 4/1989 | Grollier et al. ............... | 222/1 |
| 5,032,137 A | 7/1991 | Junino et al. ................. | 8/410 |
| 5,061,289 A | 10/1991 | Clausen et al. ............... | 8/405 |
| 5,380,340 A | 1/1995 | Neunhoeffer et al. ......... | 28/409 |
| 5,766,576 A | 6/1998 | Löwe et al. .................. | 424/62 |
| 6,099,592 A * | 8/2000 | Vidal et al. .................... | 8/409 |
| 6,099,593 A | 8/2000 | Terranova et al. ............. | 8/409 |

FOREIGN PATENT DOCUMENTS

| | | |
|---|---|---|
| DE | 23 59 399 | 6/1975 |
| DE | 38 43 892 | 6/1990 |
| DE | 41 33 957 | 4/1993 |
| DE | 195 43 988 | 5/1997 |
| EP | 0 740 931 | 11/1996 |
| FR | 2 586 913 | 3/1987 |
| FR | 2 630 438 | 10/1989 |
| FR | 2 733 749 | 11/1996 |
| FR | 2 750 048 | 12/1997 |
| GB | 1 026 978 | 4/1966 |
| GB | 1 153 196 | 5/1969 |
| JP | 2-19576 | 1/1990 |
| WO | WO 94/08969 | 4/1994 |
| WO | WO 94/08970 | 4/1994 |
| WO | WO 96/15765 | 5/1996 |
| WO | WO 97/42173 | 11/1997 |

OTHER PUBLICATIONS

E.C. Taylor et al., "Pteridines. XVI. A Synthesis of 2–Aminopyrazine–3–carboxamides by Reductive Ring Cleavage of 3–Hydroxy–1–pyrazolo[b]pyrazines", Journal of the American Chemical Society, vol. 80, No. 2, Jan. 20, 1958, pp. 421–427.
English language Derwent Abstract of JP 2–19576, Jan. 23, 1990.
English language Derwent Abstract of JP 3–10659, Jan. 18, 1991.

* cited by examiner

*Primary Examiner*—Yogendra N. Gupta
*Assistant Examiner*—Eisa B Elhilo
(74) *Attorney, Agent, or Firm*—Finnegan, Henderson, Farabow, Garrett & Dunner, L.L.P.

(57) ABSTRACT

The invention concerns novel pyrazole derivatives comprising at least a cationic group Z, Z being selected among the quaternized aliphatic chains, aliphatic chains comprising at least a saturated quaternized cycle, and aliphatic chains comprising at least an unsaturated quaternized cycle, their use as oxidation base for dyeing keratin fibres, dyeing compositions containing them, and dyeing methods using them.

36 Claims, No Drawings

CATIONIC OXIDATION BASES, THEIR USE OF DYEING KERATIN FIBRES, DYEING COMPOSITIONS AND DYEING METHODS

The invention relates to novel pyrazole derivatives containing at least one cationic group Z, Z being chosen from quaternized aliphatic chains, aliphatic chains containing at least one quaternized saturated ring and aliphatic chains containing at least one quaternized unsaturated ring, to their use as oxidation base for the oxidation dyeing of keratin fibres, to dye compositions containing them and to oxidation dyeing processes using them.

It is known practice to dye keratin fibres, and in particular human hair, with dye compositions containing oxidation dye precursors, in particular ortho- or para-phenylenediamines, ortho- or para-aminophenols and heterocyclic compounds such as diaminopyrazole derivatives, which are generally referred to as oxidation bases. The oxidation dye precursors, or oxidation bases, are colourless or weakly coloured compounds which, when combined with oxidizing products, can give rise to coloured compounds and dyes by a process of oxidative condensation.

It is also known that the shades obtained with these oxidation bases can be varied by combining them with couplers or coloration modifiers, the latter being chosen in particular from aromatic meta-diamines, meta-aminophenols, meta-diphenols and certain heterocyclic compounds.

The variety of molecules used as oxidation bases and couplers makes it possible to obtain a wide range of colours.

The so-called "permanent" coloration obtained by means of these oxidation dyes must moreover satisfy a certain number of requirements. Thus, it must have no toxicological drawbacks and it must allow shades of the desired strength to be obtained and have good resistance to external agents (light, bad weather, washing, permanent-waving, perspiration and friction).

The dyes must also allow white hairs to be covered, and, lastly, they must be as unselective as possible, i.e. they must allow the smallest possible differences in coloration to be produced over the entire length of the same keratin fibre, which may indeed be differently sensitized (i.e. damaged) between its tip and its root.

Now, the Applicant has just discovered, entirely surprisingly and unexpectedly, that novel pyrazole derivatives of formula (I) defined below, containing at least one cationic group Z, Z being chosen from quaternized aliphatic chains, aliphatic chains containing at least one quaternized saturated ring and aliphatic chains containing at least one quaternized unsaturated ring, are not only suitable for use as oxidation base, but also allow dye compositions to be obtained which lead to strong colorations, in a wide range of colours, and which have excellent properties of resistance to the various treatments to which keratin fibres may be subjected.

These discoveries form the basis of the present invention.

A first subject of the invention is thus novel compounds of formula (I) below, the addition salts thereof with an acid or with a base, and the possible tautomeric forms thereof:

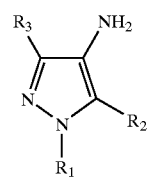

(I)

in which:

$R_1$ represents a hydrogen atom; a group Z as defined below; a $C_1$–$C_6$ alkyl radical; a $C_1$–$C_6$ trifluoroalkyl radical; a $C_1$–$C_6$ monohydroxyalkyl radical; a $C_2$–$C_6$ polyhydroxyalkyl radical; an aryl($C_1$–$C_6$)alkyl radical in which the aryl radical may be in particular a phenyl radical or a 5- or 6-membered aromatic heterocycle such as, for example, a pyridyl ring, an imidazolyl ring, a furyl ring or an oxazolyl ring; a ($C_1$–$C_6$)alkoxy($C_1$–$C_6$)alkyl radical; a ($C_1$–$C_6$)alkylthio($C_1$–$C_6$)alkyl radical; an amino($C_1$–$C_6$)alkylcarbonyl($C_1$–$C_6$)alkyl radical; an N—Z-amino($C_1$–$C_6$)alkylcarbonyl($C_1$–$C_6$)alkyl radical; an N—($C_1$–$C_6$)alkylamino($C_1$–$C_6$)alkylcarbonyl($C_1$–$C_6$)alkyl radical; an N,N-di($C_1$–$C_6$)alkylamino($C_1$–$C_6$)alkylcarbonyl($C_1$–$C_6$)alkyl radical; a $C_1$–$C_6$ aminosulphonylalkyl radical; a $C_1$–$C_6$ N—Z-aminosulphonylalkyl radical; an N—($C_1$–$C_6$)alkylaminosulphonyl($C_1$–$C_6$)alkyl radical; an N,N-di($C_1$–$C_6$)alkylaminosulphonyl($C_1$–$C_6$)alkyl radical;

$R_2$ and $R_3$, which may be identical or different, represent a group —$NHR_4$; a hydroxyl radical; a halogen atom; a nitro radical; a cyano radical; a carboxyl radical; a $C_1$–$C_6$ alkylcarboxyl radical; a carboxyaryl radical; a carbamyl radical; an N—($C_1$–$C_6$)alkylcarbamyl radical; an N,N-di($C_1$–$C_6$)alkylcarbamyl radical; an N-arylcarbamyl radical; a $C_1$–$C_6$ alkoxy radical; an aryloxy radical; a $C_1$–$C_6$ thioalkyl radical; a thioaryl radical or one of the meanings given above for $R_1$; it being understood that at least one of the radicals $R_2$ and $R_3$ represents a group —$NHR_4$ or a hydroxyl radical;

$R_4$ represents a hydrogen atom; a group Z as defined below; a $C_1$–$C_6$ alkyl radical; a $C_1$–$C_6$ monohydroxyalkyl radical; a $C_2$–$C_6$ polyhydroxyalkyl radical; a ($C_1$–$C_6$)alkoxy($C_1$–$C_6$)alkyl radical; an aryl radical; a benzyl radical; a cyano($C_1$–$C_6$)alkyl radical; a carbamyl($C_1$–$C_6$)alkyl radical; an N—($C_1$–$C_6$)alkylcarbamyl($C_1$–$C_6$)alkyl radical; an N,N-di($C_1$–$C_6$)alkylcarbamyl($C_1$–$C_6$)alkyl radical; a thiocarbamyl($C_1$–$C_6$)alkyl radical; a $C_1$–$C_6$ trifluoroalkyl radical; a $C_1$–$C_6$ sulphoalkyl radical; a ($C_1$–$C_6$)alkylcarboxy($C_1$–$C_6$)alkyl radical; a ($C_1$–$C_6$)alkylsulphinyl($C_1$–$C_6$)alkyl radical; a $C_1$–$C_6$ aminosulphonylalkyl radical; a $C_1$–$C_6$ N—Z-aminosulphonylalkyl radical; an N—($C_1$–$C_6$)alkylaminosulphonyl($C_1$–$C_6$)alkyl radical; an N,N-di($C_1$–$C_6$)alkylaminosulphonyl($C_1$–$C_6$)alkyl radical; a $C_1$–$C_6$ aminoalkyl radical; a $C_1$–$C_6$ aminoalkyl radical in which the amine is substituted with one or two radicals, which may be identical or different, chosen from $C_1$–$C_6$ alkyl, $C_1$–$C_6$ monohydroxyalkyl, $C_2$–$C_6$ polyhydroxyalkyl, ($C_1$–$C_6$)alkylcarbonyl, $C_1$–$C_6$ alkylsulphonyl, formyl and trifluoro($C_1$–$C_6$)alkylcarbonyl radicals or with a group Z; the amine of the $C_1$–$C_6$ aminoalkyl radical may also be substituted with two radicals forming, together with the nitrogen atom of the said amine, a saturated or unsaturated 5- or 6-membered ring which may contain one or more hetero atoms chosen from nitrogen, oxygen and sulphur, such as, for example, a piperidine, morpholine, imidazole or oxazole ring;

Z is chosen from the unsaturated cationic groups of formulae (II) and (III) below, and the saturated cationic groups of formula (IV) below:

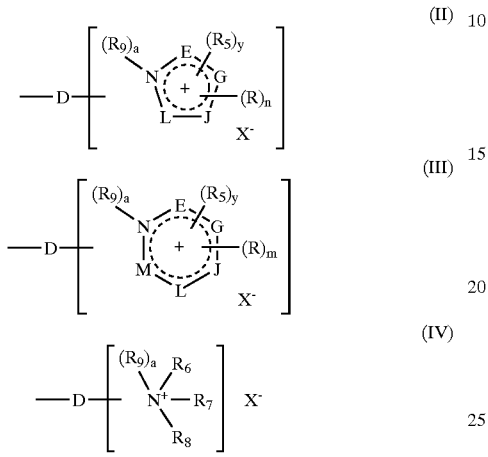

in which:

D is a linker arm which represents a linear or branched alkyl chain preferably containing from 1 to 14 carbon atoms, which can be interrupted by one or more hetero atoms such as oxygen, sulphur or nitrogen atoms, and which can be substituted with one or more hydroxyl or $C_1$–$C_6$ alkoxy radicals, and which can bear one or more ketone functions;

the ring members E, G, J, L and M, which may be identical or different, represent a carbon, oxygen, sulphur or nitrogen atom;

n is an integer between 0 and 4 inclusive;

m is an integer between 0 and 5 inclusive;

the radicals R, which may be identical or different, represent a second group Z, which is identical to or different from the first group Z, a halogen atom, a hydroxyl radical, a $C_1$–$C_6$ alkyl radical, a $C_1$–$C_6$ monohydroxyalkyl radical, a $C_2$–$C_6$ polyhydroxyalkyl radical, a nitro radical, a cyano radical, a cyano($C_1$–$C_6$)alkyl radical, a $C_1$–$C_6$ alkoxy radical, a tri($C_1$–$C_6$)alkylsilane($C_1$–$C_6$)alkyl radical, an amido radical, an aldehydo radical, a carboxyl radical, a ($C_1$–$C_6$)alkylcarbonyl radical, a thio radical, a $C_1$–$C_6$ thioalkyl radical, a $C_1$–$C_6$ alkylthio radical, an amino radical, an amino radical protected with a ($C_1$–$C_6$)alkylcarbonyl or $C_1$–$C_6$ alkylsulphonyl radical; a group NHR''' or NR''R''' in which R'' and R''', which may be identical or different, represent a $C_1$–$C_6$ alkyl radical, a $C_1$–$C_6$ monohydroxyalkyl radical or a $C_2$–$C_6$ polyhydroxyalkyl radical;

$R_5$ represents a $C_1$–$C_6$ alkyl radical, a $C_1$–$C_6$ monohydroxyalkyl radical, a $C_2$–$C_6$ polyhydroxyalkyl radical, a cyano($C_1$–$C_6$)alkyl radical, a tri($C_1$–$C_6$) alkylsilane($C_1$–$C_6$)alkyl radical, a ($C_1$–$C_6$)alkoxy ($C_1$–$C_6$)alkyl radical, a carbamyl($C_1$–$C_6$)alkyl radical, a ($C_1$–$C_6$)alkylcarboxy($C_1$–$C_6$)alkyl radical, a benzyl radical or a second group Z, which is identical to or different from the first group Z;

$R_6$, $R_7$ and $R_8$, which may be identical or different, represent a $C_1$–$C_6$ alkyl radical, a $C_1$–$C_6$ monohydroxyalkyl radical, a $C_2$–$C_6$ polyhydroxyalkyl radical, a ($C_1$–$C_6$)alkoxy($C_1$–$C_6$)alkyl radical, a cyano($C_1$–$C_6$)alkyl radical, an aryl radical, a benzyl radical, a $C_1$–$C_6$ amidoalkyl radical, a tri($C_1$–$C_6$) alkylsilane($C_1$–$C_6$)alkyl radical or a $C_1$–$C_6$ aminoalkyl radical in which the amine is protected with a ($C_1$–$C_6$)alkylcarbonyl or $C_1$–$C_6$ alkylsulphonyl radical; two of the radicals $R_6$, $R_7$ and $R_8$ can together also form, with the nitrogen atom to which they are attached, a saturated 5- or 6-membered carbon ring or a ring containing one or more hetero atoms such as, for example, a pyrrolidine ring, a piperidine ring, a piperazine ring or a morpholine ring, it being possible for the said ring to be unsubstituted or substituted with a halogen atom, a hydroxyl radical, a $C_1$–$C_6$ alkyl radical, a $C_1$–$C_6$ monohydroxyalkyl radical, a $C_2$–$C_6$ polyhydroxyalkyl radical, a nitro radical, a cyano radical, a cyano($C_1$–$C_6$)alkyl radical, a $C_1$–$C_6$ alkoxy radical, a tri($C_1$–$C_6$)alkylsilane($C_1$–$C_6$)alkyl radical, an amido radical, an aldehydo radical, a carboxyl radical, a keto($C_1$–$C_6$)alkyl radical, a thio radical, a $C_1$–$C_6$ thioalkyl radical, a $C_1$–$C_6$ alkylthio radical, an amino radical or an amino radical protected with a ($C_1$–$C_6$)alkylcarbonyl or $C_1$–$C_6$ alkylsulphonyl radical; one of the radicals $R_6$, $R_7$ and $R_8$ can also represent a second group Z which is identical to or different from the first group Z;

$R_9$ represents a $C_1$–$C_6$ alkyl radical; a $C_1$–$C_6$ monohydroxyalkyl radical; a $C_2$–$C_6$ polyhydroxyalkyl radical; an aryl radical; a benzyl radical; a $C_1$–$C_6$ aminoalkyl radical, a $C_1$–$C_6$ aminoalkyl radical in which the amine is protected with a ($C_1$–$C_6$) alkylcarbonyl or $C_1$–$C_6$ alkylsulphonyl radical; a carboxy($C_1$–$C_6$)alkyl radical; a cyano($C_1$–$C_6$)alkyl radical; a carbamyl($C_1$–$C_6$)alkyl radical; a $C_1$–$C_6$ trifluoroalkyl radical; a tri($C_1$–$C_6$)alkylsilane ($C_1$–$C_6$)alkyl radical; a $C_1$–$C_6$ sulphonamidoalkyl radical; a ($C_1$–$C_6$)alkylcarboxy($C_1$–$C_6$)alkyl radical; a ($C_1$–$C_6$)alkylsulphinyl($C_1$–$C_6$)alkyl radical; a ($C_1$–$C_6$)alkylsulphonyl($C_1$–$C_6$)alkyl radical; a ($C_1$–$C_6$)alkylketo($C_1$–$C_6$)alkyl radical; an N—($C_1$–$C_6$)alkylcarbamyl($C_1$–$C_6$)alkyl radical; an N—($C_1$–$C_6$)alkylsulphonamido($C_1$–$C_6$)alkyl radical;

a and y are integers equal to 0 or 1; with the following conditions:

in the unsaturated cationic groups of formula (II):
when a=0, the linker arm D is attached to the nitrogen atom,
when a=1, the linker arm D is attached to one of the ring members E, G, J or L,
y can take the value 1 only:
1) when the ring members E, G, J and L simultaneously represent a carbon atom and when the radical $R_5$ is borne by the nitrogen atom of the unsaturated ring; or alternatively
2) when at least one of the ring members E, G, J and L represents a nitrogen atom to which the radical $R_5$ is attached;

in the unsaturated cationic groups of formula (III):
when a=0, the linker arm D is attached to the nitrogen atom,
when a=1, the linker arm D is attached to one of the ring members E, G, J, L or M,
y can take the value 1 only when at least one of the ring members E, G, J, L and M represents a divalent atom and when the radical $R_5$ is borne by the nitrogen atom of the unsaturated ring;

in the cationic groups of formula (IV):
when a=0, then the linker arm is attached to the nitrogen atom bearing the radicals $R_6$ to $R_8$,
when a=1, then two of the radicals $R_6$ to $R_8$ form, together with the nitrogen atom to which they are attached, a saturated 5- or 6-membered ring as defined above, and the linker arm D is borne by a carbon atom of the said saturated ring;

$X^-$ represents a monovalent or divalent anion and is preferably chosen from a halogen atom such as chlorine, bromine, fluorine or iodine, a hydroxide, a hydrogenosulphate or a $C_1$–$C_6$ alkyl sulphate such as, for example, a methyl sulphate or an ethyl sulphate;

it being understood that the number of cationic groups Z is at least equal to 1.

As mentioned above, the colorations obtained with the oxidation dye composition containing one or more compounds of formula (I) in accordance with the invention are strong and produce a wide range of colours. They moreover have excellent properties of resistance to the action of various external agents (light, bad weather, washing, permanent-waving, perspiration, friction). These properties are particularly noteworthy, in particular as regards the resistance of the colorations obtained to the action of light, washings, permanent-waving and perspiration.

In formula (I) above, the alkyl and alkoxy radicals can be linear or branched.

Among the rings of the unsaturated groups Z of formula (II) above, mention may be made in particular, for example, of pyrrole, imidazole, pyrazole, oxazole, thiazole and triazole rings.

Among the rings of the unsaturated groups Z of formula (III) above, mention may be made in particular, for example, of pyridine, pyrimidine, pyrazine, oxazine and triazine rings.

When the compounds of formula (I) are such that they contain an OH group on one of the positions 3 or 5, α of a nitrogen atom, there is a tautomeric equilibrium which may be represented, for example, by the following scheme:

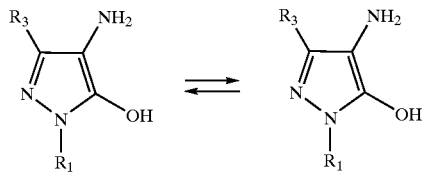

Among the compounds of formula (I) above which may be mentioned in particular are:

[3-(4-amino-2,5-dimethyl-2H-pyrazol-3-ylamino)propyl]-trimethylammonium chloride;
[3-(4-amino-2,5-dimethyl-2H-pyrazol-3-ylamino)propyl]-(2-hydroxyethyl)dimethylammonium chloride;
3-[3-(4-amino-2,5-dimethyl-2H-pyrazol-3-ylamino)-propyl]-1-(2-hydroxyethyl)-3H-imidazol-1-ium chloride;
3-[(4-amino-2H-pyrazol-3-ylcarbamoyl)methyl]-1-methyl-3H-imidazol-1-ium chloride;
3-[2-(4,5-diamino-3-methylpyrazol-1-yl)ethyl]-1-methyl-3H-imidazol-1-ium chloride;
3-[2-(4,5-diaminopyrazol-1-yl)ethyl]-1-methyl-3H-imidazol-1-ium chloride;
[2-(4,5-diamino-3-methylpyrazol-1-yl)ethyl]trimethylammonium chloride;
[2-(4,5-diaminopyrazol-1-yl)ethyl]trimethylammonium chloride;
[2-(4-amino-5-hydroxypyrazol-1-yl)ethyl]trimethylammonium chloride;
[2-(4-amino-5-hydroxy-3-methylpyrazol-1-yl)ethyl]-trimethylammonium chloride;
3-[2-(4-amino-5-hydroxy-3-methylpyrazol-1-yl)ethyl]-1-methyl-3H-imidazol-1-ium chloride;
3-[2-(4-amino-5-hydroxypyrazol-1-yl)ethyl]-1-methyl-3H-imidazol-1-ium chloride;
3-[2-(4,5-diamino-1-methyl-1H-pyrazol-3-yl)ethyl]-1-methyl-3H-imidazol-1-ium chloride, and the addition salts thereof with an acid or with a base, and the possible tautomeric forms thereof.

Among these compounds of formula (I) that are preferred more particularly are:

[3-(4-amino-2,5-dimethyl-2H-pyrazol-3-ylamino)propyl]-trimethylammonium chloride;
[3-(4-amino-2,5-dimethyl-2H-pyrazol-3-ylamino)propyl]-(2-hydroxyethyl)dimethylammonium chloride;
3-[3-(4-amino-2,5-dimethyl-2H-pyrazol-3-ylamino)-propyl]-1-(2-hydroxyethyl)-3H-imidazol-1-ium chloride;
3-[(4-amino-2H-pyrazol-3-ylcarbamoyl)methyl]-1-methyl-3H-imidazol-1-ium chloride;
3-[2-(4,5-diamino-3-methylpyrazol-1-yl)ethyl]-1-methyl-3H-imidazol-1-ium chloride;
3-[2-(4,5-diamino-1-methyl-1H-pyrazol-3-yl)ethyl]-1-methyl-3H-imidazol-1-ium chloride;

and the addition salts thereof with an acid or with a base, and the possible tautomeric forms thereof.

The compounds of formula (I) in accordance with the invention may be readily obtained according to methods that are well known in the prior art:
either by reducing the corresponding cationic nitro or nitroso compounds. In this case, the reduction to the corresponding primary aromatic amine is carried out according to conventional methods (J. Lehmman in Houben-Weyl, "Methoden der Organischen Chemie", Volume IV/1c: Reduction I pages 491 to 537, 1980). The methods that are preferred according to the invention involve metals such as Zn, Sn or Fe in acidic medium, for instance aqueous hydrochloric acid or aqueous acetic acid in the presence or absence of a co-solvent such as methanol, ethanol or tetrahydrofuran. Catalytic hydrogenation is a reduction method that is preferred according to the invention. This catalytic hydrogenation uses metals such as palladium, platinum or nickel. It is even more particularly preferred to use palladium-on-charcoal or Raney nickel, or alternatively oxides such as $PtO_2$ in solvents such as methanol, ethanol, tetrahydrofuran or ethyl acetate, in the presence or absence of an acid, for example acetic acid. These catalytic reductions may also be carried out with formic acid in the presence of a trialkylamine such as triethylamine or with an ammonium formate instead of hydrogen gas (S. Ram, R. E. Ehrenkaufer, Synthesis, 1988, 91).
or by reducing the corresponding cationic azo compounds (reductive cleavage). The reduction to the corresponding primary aromatic amine is carried out according to conventional methods (J. Lehmman in Houben-Weyl, "Methoden der Organischen Chemie", Volume IV/1c: Reduction I pages 551 to 553, 1980; E. C. Taylor & Coll., J. Amer. Chem. Soc., 80, 421, 1958).

This reduction step (production of a primary aromatic amine) which gives the synthesized compound its nature as an oxidizable compound (oxidation base), which may or may not be followed by a salification, is generally, for convenience, the final step of the synthesis.

This reduction can take place earlier in the sequence of reactions leading to the preparation of the compounds of formula (I), and according to well-known processes it is then necessary to "protect" the primary amine created (for example by an acetylation, benzenesulphonation, etc. step), then carry out the desired substitution(s) or modification(s) (including quaternization) and end by "deprotecting" (generally in acidic medium) the amine function.

When the synthesis is complete, the compounds of formula (I) in accordance with the invention can, if necessary, be recovered by methods which are well known in the state of the art, such as crystallization or distillation.

Another subject of the invention is the use of the compounds of formula (I) in accordance with the invention as oxidation bases for the oxidation dyeing of keratin fibres, and in of particular human keratin fibres such as the hair.

The invention also relates to a composition for the oxidation dyeing of keratin fibres, and in particular of human keratin fibres such as the hair, characterized in that it comprises, as an oxidation base, in a medium which is suitable for dyeing, at least one compound of formula (I) in accordance with the invention.

The compound(s) of formula (I) in accordance with the invention preferably represent(s) from 0.0005 to 12% by weight approximately relative to the total weight of the dye composition, and even more preferably from 0.005 to 6% by weight approximately relative to this weight.

The medium which is suitable for dyeing (or the support) generally consists of water or a mixture of water and at least one organic solvent to dissolve the compounds which would not be sufficiently soluble in water. As organic solvent, mention may be made, for example, of $C_1$–$C_4$ lower alkanols, such as ethanol and isopropanol; glycerol; glycols and glycol ethers such as 2-butoxyethanol, propylene glycol, propylene glycol monomethyl ether, diethylene glycol monoethyl ether and monomethyl ether, as well as aromatic alcohols such as benzyl alcohol or phenoxyethanol, similar products and mixtures thereof.

The solvents can be present in proportions preferably of between 1 and 40% by weight approximately relative to the total weight of the dye composition, and even more preferably between 5 and 30% by weight approximately.

The pH of the dye composition in accordance with the invention is generally between 3 and 12 approximately, and preferably between 5 and 11 approximately. It can be adjusted to the desired value using acidifying or basifying agents commonly used to dye keratin fibres.

Among the acidifying agents which may be mentioned, for example, are inorganic or organic acids such as hydrochloric acid, orthophosphoric acid, sulphuric acid, carboxylic acids such as acetic acid, tartaric acid, citric acid and lactic acid, and sulphonic acids.

Among the basifying agents which can be mentioned, for example, are aqueous ammonia, alkaline carbonates, alkanolamines such as mono-, di- and triethanolamine and derivatives thereof, sodium hydroxide, potassium hydroxide and the compounds of formula (V) below:

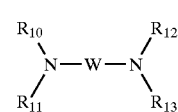
(V)

in which W is a propylene residue optionally substituted with a hydroxyl group or a $C_1$–$C_6$ alkyl radical; $R_{10}$, $R_{11}$, $R_{12}$ and $R_{13}$, which may be identical or different, represent a hydrogen atom, a $C_1$–$C_6$ alkyl radical or a $C_1$–$C_6$ hydroxyalkyl radical.

The dye composition in accordance with the invention can also contain, in addition to the compound or compounds of formula (I) defined above, at least one additional oxidation base which can be chosen from the oxidation bases conventionally used in oxidation dyeing and among which mention may be made in particular of para-phenylenediamines, bis(phenyl)alkylenediamines, para-aminophenols, ortho-aminophenols and heterocyclic bases other than the compounds of formula (I).

Among the para-phenylenediamines which can be mentioned more particularly, for example, are para-phenylenediamine, para-toluylenediamine, 2,6-dimethyl-para-phenylenediamine, 2-β-hydroxyethyl-para-phenylenediamine, 2-n-propyl-para-phenylenediamine, 2-isopropyl-para-phenylenediamine, N-(β-hydroxypropyl)-para-phenylenediamine, N,N-bis(β-hydroxyethyl)-para-phenylenediamine, 4-amino-N-(β-methoxyethyl)aniline and the para-phenylenediamines described in French patent application FR 2,630,438, and the addition salts thereof with an acid.

Among the bis(phenyl)alkylenediamines which can be mentioned more particularly, for example, are N,N'-bis(β-hydroxyethyl)-N,N'-bis(4'-aminophenyl)-1,3-diaminopropanol, N,N'-bis(β-hydroxyethyl)-N,N'-bis(4'-aminophenyl)ethylenediamine, N,N'-bis(4-aminophenyl) tetramethylenediamine, N,N'-bis(β-hydroxyethyl)-N,N'-bis(4-aminophenyl)tetramethylenediamine, N,N'-bis(4-methylaminophenyl)tetramethylenediamine and N,N'-bis(ethyl)-N,N'-bis(4'-amino-3'-methylphenyl)ethylenediamine, and the addition salts thereof with an acid.

Among the para-aminophenols which can be mentioned more particularly, for example, are para-aminophenol, 4-amino-3-methylphenol, 4-amino-3-fluorophenol, 4-amino-3-hydroxymethylphenol, 4-amino-2-methylphenol, 4-amino-2-hydroxymethylphenol, 4-amino-2-methoxymethylphenol, 4-amino-2-aminomethylphenol and 4-amino-2-(β-hydroxyethylaminomethyl)phenol, and the addition salts thereof with an acid.

Among the ortho-aminophenols which can be mentioned more particularly, for example, are 2-aminophenol, 2-amino-5-methylphenol, 2-amino-6-methylphenol and 5-acetamido-2-aminophenol, and the addition salts thereof with an acid.

Among the heterocyclic bases which can be mentioned more particularly, for example, are pyridine derivatives, pyrimidine derivatives and non-cationic pyrazole derivatives.

Among the pyridine derivatives which may be mentioned more particularly are the compounds disclosed, for example, in patents GB 1 026 978 and GB 1 153 196, such as 2,5-diaminopyridine, 2-(4-methoxyphenyl)amino-3-aminopyridine, 2,3-diamino-6-methoxypyridine, 2-(β-methoxyethyl)amino-3-amino-6-methoxypyridine and 3,4-diaminopyridine, and the addition salts thereof with an acid.

Among the pyrimidine derivatives which may be mentioned more particularly are the compounds disclosed, for example, in German patent DE 2 359 399 or Japanese patents JP 88-169 571 and JP 91-10659 or patent application WO 96/15765, such as 2,4,5,6-tetraaminopyrimidine, 4-hydroxy-2,5,6-triaminopyrimidine, 2-hydroxy-4,5,6-triaminopyrimidine, 2,4-dihydroxy-5,6-diaminopyrimidine, 2,5,6-triaminopyrimidine, and pyrazolopyrimidine derivatives such as those mentioned in patent application FR-A-2 750 048, and among which mention may be made of pyrazolo[1,5-a]pyrimidine-3,7-diamine; 2,5-dimethylpyrazolo[1,5-a]pyrimidine-3,7-diamine; pyrazolo[1,5-a]pyrimidine-3,5-diamine; 2,7-dimethylpyrazolo[1,5-a]pyrimidine-3,5-diamine; 3-aminopyrazolo[1,5-a]pyrimidine-7-ol; 3-aminopyrazolo[1,5-a]-pyrimidin-5-ol; 2-(3-aminopyrazolo[1,5-a]pyrimidin-7-ylamino)ethanol, 2-(7-aminopyrazolo[1,5-a]pyrimidin-3-ylamino)ethanol, 2-[(3-aminopyrazolo[1,5-a]pyrimidin-7-yl)-(2-hydroxyethyl)amino]ethanol, 2-[(7-aminopyrazolo[1,5-a]pyrimidin-3-yl)-(2-hydroxyethyl)amino]ethanol, 5,6-dimethylpyrazolo[1,5-a]pyrimidine-3,7-diamine, 2,6-dimethylpyrazolo[1,5-a]pyrimidine-3,7-diamine, 2,5,N7,N7-tetramethylpyrazolo[1,5-a]pyrimidine-3,7-diamine and 3-amino-5-methyl-7-imidazolylpropylaminopyrazolo[1,5-a]pyrimidine, the possible tautomeric forms thereof, and the addition salts thereof with an acid.

Among the non-cationic pyrazole derivatives which may be mentioned more particularly are the compounds disclosed in patents DE 3 843 892 and DE 4 133 957 and patent applications WO 94/08969, WO 94/08970, FR-A-2 733 749 and DE 195 43 988, such as 4,5-diamino-1-methylpyrazole, 3,4-diaminopyrazole, 4,5-diamino-1-(4'-chlorobenzyl)pyrazole, 4,5-diamino-1,3-dimethylpyrazole, 4,5-diamino-3-methyl-1-phenylpyrazole, 4,5-diamino-1-methyl-3-phenylpyrazole, 4-amino-1,3-dimethyl-5-hydrazinopyrazole, 1-benzyl-4,5-diamino-3-methylpyrazole, 4,5-diamino-3-tert-butyl-1-methylpyrazole, 4,5-diamino-1-tert-butyl-3-methylpyrazole, 4,5-diamino-1-(β-hydroxyethyl)-3-methylpyrazole, 4,5-diamino-1-ethyl-3-methylpyrazole, 4,5-diamino-1-ethyl-3-(4'-methoxyphenyl)pyrazole, 4,5-diamino-1-ethyl-3-hydroxymethylpyrazole, 4,5-diamino-3-hydroxymethyl-1-methylpyrazole, 4,5-diamino-3-hydroxymethyl-1-isopropylpyrazole, 4,5-diamino-3-methyl-1-isopropylpyrazole, 4-amino-5-(2'-aminoethyl)amino-1,3-dimethylpyrazole, 3,4,5-triaminopyrazole, 1-methyl-3,4,5-triaminopyrazole and 3,5-diamino-1-methyl-4-methylaminopyrazole, 3,5-diamino-4-(β-hydroxyethyl)amino-1-methylpyrazole, and the addition salts thereof with an acid.

When they are used, these additional oxidation bases preferably represent from 0.0005 to 12% by weight approximately relative to the total weight of the dye composition, and even more preferably from 0.005 to 6% by weight approximately relative to this weight.

The oxidation dye compositions in accordance with the invention can also contain at least one coupler and/or at least one direct dye, in particular in order to modify the shades or to enrich them with glints.

The couplers which can be used in the oxidation dye compositions in accordance with the invention can be chosen from the couplers used conventionally in oxidation dyeing and among which mention may be made in particular of meta-phenylenediamines, meta-aminophenols, meta-diphenols and heterocyclic couplers such as, for example, indole derivatives, indolene derivatives, pyridine derivatives and pyrazolones, and the addition salts thereof with an acid.

These couplers are chosen more particularly from 2-methyl-5-aminophenol, 5-N-(β-hydroxyethyl)amino-2-methylphenol, 3-aminophenol, 1,3-dihydroxybenzene, 1,3-dihydroxy-2-methylbenzene, 4-chloro-1,3-dihydroxybenzene, 2,4-diamino-1-(β-hydroxyethyloxy)benzene, 2-amino-4-(β-hydroxyethylamino)-1-methoxybenzene, 1,3-diaminobenzene, 1,3-bis(2,4-diaminophenoxy)propane, sesamol, α-naphthol, 6-hydroxyindole, 4-hydroxyindole, 4-hydroxy-N-methylindole, 6-hydroxyindoline, 2,6-dihydroxy-4-methylpyridine, 1H-3-methylpyrazol-5-one and 1-phenyl-3-methylpyrazol-5-one, and the addition salts thereof with an acid.

When they are present, these couplers preferably represent from 0.0001 to 10% by weight approximately relative to the total weight of the dye composition and even more preferably from 0.005 to 5% by weight approximately relative to this weight.

In general, the addition salts with an acid which can be used in the context of the invention (compounds of formula (I), additional oxidation bases and couplers) are chosen in particular from the hydrochlorides, hydrobromides, sulphates, citrates, succinates, tartrates, lactates and acetates. The addition salts with a base which may be used in the context of the invention (compounds of formula (I)) are in particular those obtained with sodium hydroxide, potassium hydroxide, aqueous ammonia or amines.

The dye composition in accordance with the invention can also contain various adjuvants conventionally used in compositions for dyeing the hair, such as anionic, cationic, nonionic, amphoteric or zwitterionic surfactants or mixtures thereof, anionic, cationic, nonionic, amphoteric or zwitterionic polymers or mixtures thereof, inorganic or organic thickeners, antioxidants, penetration agents, sequestering agents, fragrances, buffers, dispersing agents, conditioners such as, for example, silicones, film-forming agents, preserving agents and opacifiers.

Needless to say, a person skilled in the art will take care to select this or these optional additional compounds such that the advantageous properties intrinsically associated with the oxidation dye composition in accordance with the invention are not, or are not substantially, adversely affected by the addition(s) envisaged.

The dye composition according to the invention can be in various forms, such as in the form of liquids, creams or gels or in any other form which is suitable for dyeing keratin fibres, and in particular human hair.

The invention also relates to a process for dyeing keratin fibres, and in particular human keratin fibres such as the hair, using the dye composition as defined above.

According to this process, at least one dye composition as defined above is applied to the fibres, the colour being developed at acidic, neutral or alkaline pH using an oxidizing agent which is added to the dye composition just at the time of use, or which is present in an oxidizing composition which is applied simultaneously or sequentially in a separate manner.

According to a preferred embodiment of the dyeing process of the invention, the dye composition described above is preferably mixed, at the time of use, with an oxidizing composition containing, in a medium which is suitable for dyeing, at least one oxidizing agent present in an amount which is sufficient to develop a coloration. The mixture obtained is then applied to the keratin fibres and is left in place for 3 to 50 minutes approximately, preferably 5 to 30 minutes approximately, after which the fibres are rinsed, washed with shampoo, rinsed again and dried.

The oxidizing agent can be chosen from the oxidizing agents conventionally used for the oxidation dyeing of keratin fibres, and among which mention may be made of hydrogen peroxide, urea peroxide, alkali metal bromates and persalts such as perborates and persulphates, and enzymes such as peroxidases, laccases, tyrosinases and oxidoreductases, among which mention may be made in particular of pyranose oxidases, glucose oxidases, glycerol oxidases, lactate oxidases, pyruvate oxidases and uricases.

The pH of the oxidizing composition containing the oxidizing agent as defined above is such that, after mixing with the dye composition, the pH of the resultant composition applied to the keratin fibres preferably varies between 3 and 12 approximately, and even more preferably between 5 and 11. It is adjusted to the desired value using acidifying or basifying agents commonly used to dye keratin fibres and as defined above.

The oxidizing composition as defined above can also contain various adjuvants conventionally used in compositions for dyeing the hair and as defined above.

The composition which is finally applied to the keratin fibres can be in various forms, such as in the form of liquids, creams or gels or any other form which is suitable for dyeing keratin fibres, and in particular human hair.

Another subject of the invention is a multi-compartment dyeing device or "kit" or any other multi-compartment packaging system, a first compartment of which contains the dye composition as defined above and a second compartment of which contains the oxidizing composition as defined above. These devices can be equipped with a means for delivering the desired mixture onto the hair, such as the devices described in patent FR 2,586,913 in the name of the Applicant.

The examples which follow are intended to illustrate the invention without, however, limiting its scope.

PREPARATION EXAMPLES

Preparation Example 1

Synthesis of 3-[3-(4-amino-2,5-dimethyl-2H-pyrazol-3-ylamino)propyl]-1-(2-hydroxyethyl)-3H-imidazol-1-ium chloride dihydrochloride

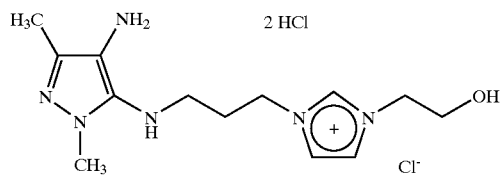

a) Preparation of (2,5-dimethyl-4-nitro-2H-pyrazol-3-yl)(3-imidazol-1-ylpropyl)amine

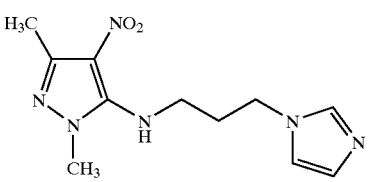

0.88 g of 5-chloro-1,3-dimethyl-4-nitro-1H-pyrazole (Aldrich), 1 molar equivalent of triethylamine, 1.1 molar equivalents of 3-imidazol-1-ylpropylamine and 5 ml of N,N-dimethylformamide were introduced into a 25 ml three-necked round-bottomed flask equipped with a magnetic stirrer, a thermometer and a condenser. The reaction medium was maintained at a temperature of about 105° C. for 6 hours. The solvent was evaporated off under vacuum. A black liquid was obtained, which was purified by chromatography on silica gel (ethyl acetate/methanol=4/1). 0.75 g of (2,5-dimethyl-4-nitro-2H-pyrazol-3-yl)(3-imidazol-1-ylpropyl)amine was obtained in the form of white crystals in a yield of 56.7%.

b) Preparation of 3-[3-(2,5-dimethyl-4-nitro-2H-pyrazol-3-ylamino)propyl]-1-(2-hydroxyethyl)-3H-imidazol-1-ium chloride

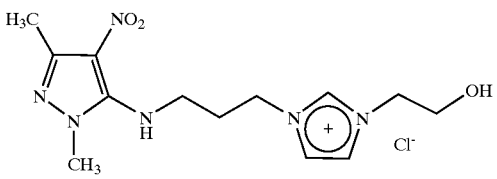

0.57 g of (2,5-dimethyl-4-nitro-2H-pyrazol-3-yl)(3-imidazol-1-ylpropyln)amine and 2.2 g of 2-chloroethanol were introduced into a 10 ml three-necked round-bottomed flask equipped with a magnetic stirrer, a thermometer and a condenser. The reaction medium was refluxed for 2 hours. The solvent was evaporated off under vacuum. 0.7 g of 3-[3-(2,5-dimethyl-4-nitro-2H-pyrazol-3-ylamino)propyl]-1-(2-hydroxyethyl)-3H-imidazol-1-ium chloride was obtained in the form of a viscous liquid, in a yield of 96%.

(c) Preparation of 3-[3-(4-amino-2,5-dimethyl-2H-pyrazol-3-ylamino)propyl]-1-(2-hydroxyethyl)-3H-midazol-1-ium chloride dihydrochloride

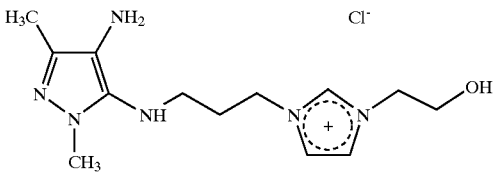

7.9 g of 3-[3-(2,5-dimethyl-4-nitro-2H-yrazol-3-ylamino)propyl]-1-(2-hydroxyethyl)-3H-imidazol-1-ium chloride obtained above in the preceding step, 150 ml of methanol and 0.97 g of 5% palladium-on-charcoal containing about 50% water were introduced into a 500 ml hydrogenation reactor. A hydrogen pressure of 10 bar was established and the reaction medium was brought to 115° C. After 5 hours, the catalyst was filtered off through Celite over 100 ml of a hydrochloric ethanol solution at a concentration of 5 mol/litre. The solvent was evaporated off under vacuum using a vane pump (0.1 bar). 6.5 g of 3-[3-(4-amino-2,5-dimethyl-2H-pyrazol-3-ylamino)propyl]-1-(2-hydroxyethyl)-3H-imidazol-1-ium chloride dihydrochloride were obtained in the form of a solid, in a yield of 73%.

The $^1$H NMR analysis ($d_6$-DMSO+$CD_3OD$) was as follows: 2.03 (m; 2H); 2.13 (s; 3H); 3.03 (t; 2H); 3.57 (s; 3H); 3.72 (t; 2H); 4.24 (t; 2H); 4.34 (t; 2H); 7.73 (dd; 1H); 9.33 (s; 1H).

Preparation Example 2

Synthesis of [3-(4-amino-2,5-dimethyl-2H-pyrazol-3-ylamino)propyl](2-hydroxyethyl) dimethylammonium chloride dihydrochloride

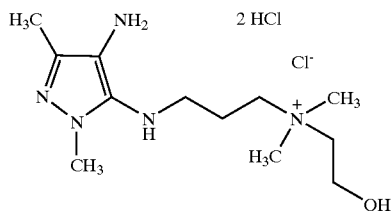

a) Preparation of [3-(2,5-dimethyl-4-nitro-2H-pyrazol-3-ylamino)propyl](2-hydroxyethyl)dimethylammonium chloride

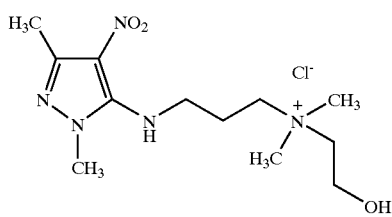

0.5 g of N-(2,5-dimethyl-4-nitro-2H-pyrazol-3-yl)-N',N'-dimethylpropane-1,3-diamine and 2.2 g of 2-chloroethanol were introduced into a 10 ml three-necked round-bottomed flask equipped with a magnetic stirrer, a thermometer and a condenser. The reaction medium was maintained at reflux for 2 hours. The medium was cooled to room temperature and diluted with 50 ml of ethyl acetate. The precipitate was filtered off. 0.55 g of [3-(2,5-dimethyl-4-nitro-2H-pyrazol-3-yl-amino)propyl](2-hydroxyethyl)dimethylammonium chloride was obtained in the form of yellow crystals, in a yield of 82%.

b) Preparation of [3-(4-amino-2,5-dimethyl-2H-pyrazol-3-ylamino)-propyl](2-hydroxyethyl)dimethylammonium chloride dihydrochloride 3.22 g of dimethylammonium chloride, 150 ml of methanol and 0.42 g of 5% palladium-on-charcoal containing about 50% water were introduced into a 250 ml hydrogenation reactor. The reactor was subjected to a hydrogen pressure of 11.7 bar and the reaction medium was brought to 60° C. After 2 hours, the hydrogen pressure was 8.3 bar. The catalyst was filtered off through Celite. A stream of hydrogen chloride gas was passed through the filtrate and the solvent was evaporated off under vacuum. 3 g of a viscous liquid were obtained, and were diluted in 100 ml of water and then freeze-dried. 1.54 g of [3-(4-amino-2,5-dimethyl-2H-pyrazol-3-ylamino)propyl](2-hydroxyethyl) dimethylammonium chloride dihydrochloride (containing 1.3 mol of water) were obtained in the form of a solid, in a yield of 40%, the elemental analysis of which, calculated for $C_{12}H_{26}N_5O.Cl.2HCl.1.3H_2O$ (MW=388.15 g/mol), was as follows:

| % | C | H | N | O | Cl |
|---|---|---|---|---|---|
| Calculated | 37.09 | 7.88 | 18.03 | 9.48 | 27.43 |
| Found | 37.46 | 7.88 | 17.79 | 9.68 | 26.85 |

APPLICATION EXAMPLES

Examples 1 to 8 of Dyeing in Basic Medium

The following dye compositions were prepared (contents in grams):

| EXAMPLE | 1 | 2 | 3 | 4 | 5 | 6 | 7 | 8 |
|---|---|---|---|---|---|---|---|---|
| [3-(4-Amino-2,5-dimethyl-2H-pyrazol-3-yl-amino)propyl](2-hydroxyethyl)dimethyl-ammonium chloride dihydrochloride (compound of formula (I)) | 1.09 | 1.09 | 1.09 | 1.09 | 1.09 | 1.09 | 1.09 | 1.09 |
| 1,3-Dihydroxybenzene (coupler) | — | 0.33 | — | — | — | — | — | — |
| 3-Aminophenol (coupler) | — | — | 0.327 | — | — | — | — | — |
| 6-Hydroxyindole (coupler) | — | — | — | 0.399 | — | — | — | — |
| 5-N-(β-Hydroxyethyl)amino-2-methylphenol (coupler) | — | — | — | — | 0.504 | — | — | — |
| 2,4-Diamino-1-(β-hydroxyethyloxy)benzene dihydrochloride (coupler) | — | — | — | — | — | 0.723 | — | — |
| 4-Hydroxyindole (coupler) | — | — | — | — | — | — | 0.399 | — |
| 3-Amino-2-chloro-6-methylphenol (coupler) | — | — | — | — | — | — | — | 0.48 |
| Common dye support No. 1 | (*) | (*) | (*) | (*) | (*) | (*) | (*) | (*) |
| Demineralized water qs | 100 g | 100 g | 100 g | 100 g | 100 g | 100 g | 100 g | 100 g |

(*) Common dye support No. 1:

| | |
|---|---|
| 96° Ethyl alcohol | 18 g |
| Sodium metabisulphite as an aqueous solution containing 35% | 0.68 g |
| Pentasodium salt of diethylenetriamino-pentaacetic acid | 1.1 g |
| 20% Aqueous ammonia | 10.0 g |

At the time of use, each of the above dye compositions was mixed, weight for weight, with a 20-volumes hydrogen peroxide solution (6% by weight) of pH 3.

The mixture obtained was applied to locks of permanent-waved grey hair containing 90% white hairs, for 30 minutes. The locks were then rinsed, washed with a standard shampoo, rinsed again and then dried.

The shades obtained are given in the table

| EXAMPLE | Dyeing pH | Shade obtained |
|---------|-----------|----------------|
| 1 | 10 ± 0.2 | Light ash-violet |
| 2 | 10 ± 0.2 | Slightly iridescent golden ash light blond |
| 3 | 10 ± 0.2 | Ash-violet |
| 4 | 10 ± 0.2 | Ash-chestnut dark blond |
| 5 | 10 ± 0.2 | Violet iridescent light chestnut |
| 6 | 10 ± 0.2 | Deep green-blue |
| 7 | 10 ± 0.2 | Violet-ash chestnut |
| 8 | 10 ± 0.2 | Violet |

Examples 9 to 12 of Dyeing in Neutral Medium

The following dye compositions were prepared (contents in grams):

| EXAMPLE | 9 | 10 | 11 | 12 |
|---------|------|------|------|------|
| [3-(4-Amino-2,5-dimethyl-2H-pyrazol-3-ylamino)-propyl] (2-hydroxyethyl)-dimethylammonium chloride dihydrochloride (compound of formula (I)) | 1.09 | 1.09 | 1.09 | 1.09 |
| 5-N-(β-Hydroxyethyl)amino-2-methylphenol (coupler) | 0.504 | — | — | — |
| 2,4-Diamino-1-(β-hydroxyethyloxy)benzene dihydrochloride (coupler) | — | 0.723 | — | — |
| 6-Hydroxyindole (coupler) | — | — | 0.399 | — |
| 4-Hydroxyindole (coupler) | — | — | — | 0.399 |
| Common dye support No. 2 | () | () | () | () |
| Demineralized water qs | 100 g | 100 g | 100 g | 100 g |

(**) Common dye support No. 2:
96° ethanol 18 g
$K_2HPO_4/KH_2PO_4$ buffer (1.5 M/1 M) 10 g
Sodium metabisulphite 0.68 g
Pentasodium salt of diethylenetriamine-pentaacetic acid 1.1 g At the time of use, each of the above dye compositions was mixed, weight for weight, with a 20-volumes hydrogen peroxide solution (6% by weight) of pH 3.

The mixture obtained was applied to locks of natural grey hair containing 90% white hairs, for 30 minutes. The locks were then rinsed, washed with a standard shampoo, rinsed again and then dried.

The shades obtained are given in the table below:

| EXAMPLE | Dyeing pH | Shade obtained |
|---------|-----------|----------------|
| 9 | 5.7 ± 0.2 | Ash-violet |
| 10 | 5.7 ± 0.2 | Green |
| 11 | 5.7 ± 0.2 | Slightly violet light blond |
| 12 | 5.7 ± 0.2 | Light red-violet |

What is claimed is:

1. A composition for oxidation dyeing of keratin fibres, wherein said composition comprises at least one oxidation base, in a medium which is suitable for dyeing, wherein said at least one oxidation base is chosen from compounds of formula (I):

acid addition salts thereof, base addition salts thereof, and tautomeric forms thereof:

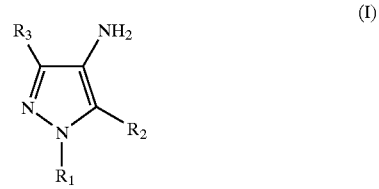

(I)

wherein:
$R_1$ is chosen from hydrogen; Z groups, as defined below; $C_1$–$C_6$ alkyl radicals; $C_1$–$C_6$ trifluoroalkyl radicals; $C_1$–$C_6$ monohydroxyalkyl radicals; $C_2$–$C_6$ polyhydroxyalkyl radicals; aryl($C_1$–$C_6$)alkyl radicals; ($C_1$–$C_6$)alkoxy($C_1$–$C_6$)alkyl radicals; ($C_1$–$C_6$) alkylthio($C_1$–$C_6$)alkyl radicals; amino($C_1$–$C_6$) alkylcarbonyl($C_1$–$C_6$)alkyl radicals; N—Z-amino ($C_1$–$C_6$)alkylcarbonyl($C_1$–$C_6$)alkyl radicals; N—($C_1$–$C_6$)alkylamino($C_1$–$C_6$)alkylcarbonyl ($C_1$–$C_6$)alkyl radicals; N,N-di($C_1$–$C_6$)alkylamino ($C_1$–$C_6$)alkylcarbonyl($C_1$–$C_6$)alkyl radicals; $C_1$–$C_6$ aminosulphonylalkyl radicals; $C_1$–$C_6$ N—Z-aminosulphonylalkyl radicals; N—($C_1$–$C_6$) alkylaminosulphonyl($C_1$–$C_6$)alkyl radicals; and N,N-di($C_1$–$C_6$)alkylaminosulphonyl($C_1$–$C_6$)alkyl radicals;

$R_2$ and $R_3$, which may be identical or different, are each chosen from —$NHR_4$ groups; hydroxyl radicals; halogens; nitro radicals; cyano radicals; carboxyl radicals; $C_1$–$C_6$ alkylcarboxyl radicals; carboxyaryl radicals; carbamyl radicals; N—($C_1$–$C_6$) alkylcarbamyl radicals; N,N-di($C_1$–$C_6$) alkylcarbamyl radicals; N-arylcarbamyl radicals; $C_1$–$C_6$ alkoxy radicals; aryloxy radicals; $C_1$–$C_6$ thioalkyl radicals; thioaryl radicals and $R_1$; with the proviso that at least one of $R_2$ and $R_3$ is chosen from —$NHR_4$ groups and a hydroxyl radicals;

$R_4$ is chosen from hydrogen; Z groups as defined below; $C_1$–$C_6$ alkyl radicals; $C_1$–$C_6$ monohydroxyalkyl radicals; $C_2$–$C_6$ polyhydroxyalkyl radicals; ($C_1$–$C_6$)alkoxy($C_1$–$C_6$)alkyl radicals; aryl radicals; benzyl radicals; cyano($C_1$–$C_6$)alkyl radicals; carbamyl($C_1$–$C_6$)alkyl radicals; N—($C_1$–$C_6$) alkylcarbamyl($C_1$–$C_6$)alkyl radicals; N,N-di($C_1$–$C_6$) alkylcarbamyl($C_1$–$C_6$)alkyl radicals; thiocarbamyl ($C_1$–$C_6$)alkyl radicals; $C_1$–$C_6$ trifluoroalkyl radicals; $C_1$–$C_6$ sulphoalkyl radicals; ($C_1$–$C_6$)alkylcarboxy ($C_1$–$C_6$)alkyl radicals; ($C_1$–$C_6$)alkylsulphinyl ($C_1$–$C_6$)alkyl radicals; $C_1$–$C_6$ aminosulphonylalkyl radicals; $C_1$–$C_6$ N—Z-aminosulphonylalkyl radicals; N—($C_1$–$C_6$)alkylaminosulphonyl($C_1$–$C_6$)alkyl radicals; N,N-di($C_1$–$C_6$)alkylaminosulphonyl ($C_1$–$C_6$)alkyl radicals; $C_1$–$C_6$ aminoalkyl radicals; $C_1$–$C_6$ aminoalkyl radicals wherein the amine is substituted with one or two radicals, which may be identical or different, chosen from $C_1$–$C_6$ alkyls, $C_1$–$C_6$ monohydroxyalkyls, $C_2$–$C_6$ polyhydroxyalkyls, ($C_1$–$C_6$)alkylcarbonyls, $C_1$–$C_6$ alkylsulphonyls, formyls, trifluoro($C_1$–$C_6$) alkylcarbonyl radicals and Z groups, and further wherein the amine of the $C_1$–$C_6$ aminoalkyl radicals may also be substituted with two radicals forming, together with the nitrogen of said amine, at least one saturated or unsaturated 5- and 6-membered rings which may contain at least one additional hetero atom chosen from nitrogen, oxygen and sulphur;

Z groups, which may be identical or different, are each chosen from groups of formulae (II), (III), and (IV) below:

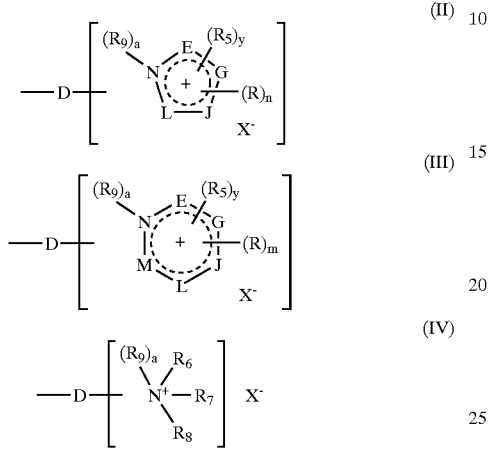

wherein:

D is a linker arm chosen from linear and branched divalent alkyl chains wherein said linear and branched alkyl chains can be interrupted by at least one hetero atom and further wherein said linear and branched alkyl divalent chains can be substituted with at least one radical and further wherein said linear and branched divalent alkyl chains can bear at least one ketone function;

the ring members E, G, J, L and M, which may be identical or different, are each chosen from carbon, oxygen, sulphur and nitrogen;

n is an integer ranging from 0 to 4;

m is an integer ranging from 0 to 5;

R, which may be identical or different, are each chosen from Z groups, halogens, hydroxyl radicals, $C_1$–$C_6$ alkyl radicals, $C_1$–$C_6$ monohydroxyalkyl radicals, $C_2$–$C_6$ polyhydroxyalkyl radicals, nitro radicals, cyano radicals, cyano($C_1$–$C_6$)alkyl radicals, $C_1$–$C_6$ alkoxy radicals, tri($C_1$–$C_6$)alkylsilane($C_1$–$C_6$)alkyl radicals, amido radicals, aldehydo radicals, carboxyl radicals, ($C_1$–$C_6$)alkylcarbonyl radicals, thio radicals, $C_1$–$C_6$ thioalkyl radicals, $C_1$–$C_6$ alkylthio radicals, amino radicals, amino radicals protected with at least one radical chosen from ($C_1$–$C_6$) alkylcarbonyl radicals and $C_1$–$C_6$ alkylsulphonyl radicals; NHR" groups and NR"R'" groups wherein R" and R'", which may be identical or different, are each chosen from $C_1$–$C_6$ alkyl radicals, $C_1$–$C_6$ monohydroxyalkyl radicals and $C_2$–$C_6$ polyhydroxyalkyl radicals;

$R_5$ is chosen from $C_1$–$C_6$ alkyl radicals, $C_1$–$C_6$ monohydroxyalkyl radicals, $C_2$–$C_6$ polyhydroxyalkyl radicals, cyano($C_1$–$C_6$)alkyl radicals, tri($C_1$–$C_6$)alkylsilane($C_1$–$C_6$)alkyl radicals, ($C_1$–$C_6$)alkoxy($C_1$–$C_6$)alkyl radicals, carbamyl($C_1$–$C_6$) alkyl radicals, ($C_1$–$C_6$)alkylcarboxy($C_1$–$C_6$)alkyl radicals, benzyl radicals and Z groups.

$R_6$, $R_7$ and $R_8$, which may be identical or different, are each chosen from $C_1$–$C_6$ alkyl radicals, $C_1$–$C_6$ monohydroxyalkyl radicals, $C_2$–$C_6$ polyhydroxyalkyl radicals, ($C_1$–$C_6$)alkoxy($C_1$–$C_6$)alkyl radicals, cyano($C_1$–$C_6$)alkyl radicals, aryl radicals, benzyl radicals, $C_1$–$C_6$ amidoalkyl radicals, tri($C_1$–$C_6$)alkylsilane($C_1$–$C_6$)alkyl radicals and $C_1$–$C_6$ aminoalkyl radicals wherein the amine is protected with at least one radical chosen from ($C_1$–$C_6$)alkylcarbonyl radicals and $C_1$–$C_6$ alkylsulphonyl radicals;

at least two of the radicals $R_6$, $R_7$ and $R_8$ can together also form, with the nitrogen to which they are attached, at least one saturated ring chosen from saturated 5- and and 6-membered rings and rings comprising at least one additional hetero atom, wherein said at least one saturated ring is optionally substituted with at least one entity chosen from halogens, hydroxyl radicals, $C_1$–$C_6$ alkyl radicals, $C_1$–$C_6$ monohydroxyalkyl radicals, $C_2$–$C_6$ polyhydroxyalkyl radicals, nitro radicals, cyano radicals, cyano($C_1$–$C_6$)alkyl radicals, $C_1$–$C_6$ alkoxy radicals, tri($C_1$–$C_6$)alkylsilane ($C_1$–$C_6$)alkyl radicals, amido radicals, aldehydo radicals, carboxyl radicals, keto($C_1$–$C_6$)alkyl radicals, thio radicals, $C_1$–$C_6$ thioalkyl radicals, $C_1$–$C_6$ alkylthio radicals, amino radicals, and amino radicals protected with at least one radical chosen from ($C_1$–$C_6$)alkylcarbonyls and $C_1$–$C_6$ alkylsulphonyl radicals; with the proviso that one of $R_6$, $R_7$, and $R_8$ may also be chosen from Z groups.

$R_9$ is chosen from $C_1$–$C_6$ alkyl radicals; $C_1$–$C_6$ monohydroxyalkyl radicals; $C_2$–$C_6$ polyhydroxyalkyl radicals; aryl radicals; benzyl radicals; $C_1$–$C_6$ aminoalkyl radicals, $C_1$–$C_6$ aminoalkyl radicals wherein the amine is protected with at least one radical chosen from ($C_1$–$C_6$) alkylcarbonyl radicals and $C_1$–$C_6$ alkylsulphonyl radicals; carboxy($C_1$–$C_6$)alkyl radicals; cyano ($C_1$–$C_6$)alkyl radicals; carbamyl($C_1$–$C_6$)alkyl radicals; $C_1$–$C_6$ trifluoroalkyl radicals; tri($C_1$–$C_6$) alkylsilane($C_1$–$C_6$)alkyl radicals; $C_1$–$C_6$ sulphonamidoalkyl radicals; ($C_1$–$C_6$)alkylcarboxy ($C_1$–$C_6$)alkyl radicals; ($C_1$–$C_6$)alkylsulphinyl ($C_1$–$C_6$)alkyl radicals; ($C_1$–$C_6$)alkylsulphonyl ($C_1$–$C_6$)alkyl radicals; ($C_1$–$C_6$)alkylketo($C_1$–$C_6$) alkyl radicals; N—($C_1$–$C_6$)alkylcarbamyl($C_1$–$C_6$) alkyl radicals; and N—($C_1$–$C_6$) alkylsulphonamido($C_1$–$C_6$)alkyl radicals;

a and y are integers equal to 0 or 1;

with the proviso that in the unsaturated cationic groups of formula (II):

when a=0, the linker arm D is attached to a nitrogen, with the proviso that said nitrogen is not chosen from E, G, J, and L.

when a=1, the linker arm D is attached to one of the ring members chosen from E, G, J and L, and y=1 when:

1) the ring members E, G, J and L are simultaneously chosen from carbons and the radical $R_5$ is borne by the nitrogen of the unsaturated ring of said groups of formula (II) and a=0; or 2) at least one of the ring members E, G, J and L is chosen from nitrogen and said radical $R_5$ is attached to said at least one ring member;

with the proviso that in the unsaturated cationic groups of formula (III):

when a=0, the linker arm D is attached to the nitrogen, with the proviso that said nitrogen is not chosen from E, G, J, and L.

when a=1, the linker arm D is attached to one of the ring members E, G, J, L or M, y=1 when at least one of the ring members E, G, J, L and M is chosen from divalent atoms and when the radical $R_5$ is borne by the nitrogen of the unsaturated ring of formula (III);

with the proviso that in the cationic groups of formula (IV):

when a=0, then the linker arm is attached to the nitrogen bearing the radicals $R_6$, $R_7$, and $R_8$, when a=1, then two of the radicals chosen from $R_6$, $R_7$, and $R_8$ form, together with the nitrogen to which they are attached, at least one ring chosen from 5- and 6-membered saturated rings as defined above, and the linker arm D is borne by a carbon of said saturated ring;

$X^-$ is chosen from monovalent anions and divalent anions;

with the proviso that said compound of formula (I), acid additional salt, base addition salt, or tautomeric form comprises at least one Z group.

2. A composition according to claim 1, wherein said medium is chosen from water and at least one organic solvent.

3. A composition according to claim 1, wherein said medium is present in an amount ranging from 1% to 40% by weight relative to the total weight of said composition.

4. A composition according to claim 3, wherein said medium is present in an amount ranging from 5% to 30% by weight relative to the total weight of said composition.

5. A composition according to claim 1, wherein said composition has a pH ranging from 3 to 12.

6. A composition according to claim 5, wherein said composition has a pH ranging from 5 to 11.

7. A composition according to claims 1, further comprising at least one adjuvant chosen from anionic surfactants, cationic surfactants, nonionic surfactants, amphoteric surfactants, zwitterionic surfactants, anionic polymers, cationic polymers, nonionic polymers, amphoteric polymers, zwitterionic polymers, inorganic thickeners, organic thickeners, antioxidants, penetration agents, sequestering agents, fragrances, buffers, dispersing agents, silicones, film-forming agents, preserving agents and opacifiers.

8. A composition according to claim 1, wherein said composition is in the form of a liquid, a cream, or a gel.

9. A composition according to claim 1, wherein said at least one oxidation base is present in said composition in an amount ranging from 0.0005% to 12% by weight relative to the total weight of said composition.

10. A composition according to claim 9, wherein said at least one oxidation base is present in said composition in an amount ranging from 0.005% to 6% by weight relative to the total weight of the dye composition.

11. A composition according to claim 1, wherein said composition comprises at least one additional oxidation base chosen from para-phenylenediamines, bis(phenyl) alkylenediamines, para-aminophenols, ortho-aminophenols and heterocyclic bases other than the compounds of formula (I).

12. A composition according to claim 11 wherein said heterocyclic bases are chosen from pyridine derivatives, pyrimidin derivatives, and non-cationic pyrazole derivatives.

13. A composition according to claim 11, wherein said at least one additional oxidation base is present in said composition in an amount ranging from 0.0005% to 12% by weight relative to the total weight of the dye composition.

14. A composition according to claim 1, wherein said composition further comprises at least one coupler.

15. A composition according to claim 1, wherein said composition further comprises at least one direct dye.

16. A composition according to claim 14, wherein said at least one coupler is chosen from meta-phenylenediamines, meta-aminophenols, meta-diphenols and heterocyclic couplers, and acid addition salts thereof.

17. A composition according to claim 16, wherein said heterocyclic couplers are chosen from indole derivatives, indolene derivatives, pyridine derivatives, pyrazolones, and addition salts thereof.

18. A composition according to claim 14, wherein said at least one coupler is chosen from 2-methyl-5-aminophenol, 5-N-(β-hydroxyethyl)amino-2-methylphenol, 3-aminophenol, 1,3-dihydroxybenzene, 1,3-dihydroxy-2-methylbenzene, 4-chloro-1,3-dihydroxybenzene, 2,4-diamino-1-(β-hydroxyethyloxy)benzene, 2-amino-4-(β-hydroxyethylamino)-1-methoxybenzene, 1,3-diaminobenzene, 1,3-bis(2,4-diaminophenoxy)propane, sesamol, α-naphthol, 6-hydroxyindole, 4-hydroxyindole, 4-hydroxy-N-methylindole, 6-hydroxyindoline, 2,6-dihydroxy-4-methylpyridine, 1H-3-methylpyrazol-5-one and 1-phenyl-3-methylpyrazol-5-one, and acid addition salts thereof.

19. A composition according to claim 14, wherein said at least one coupler is present in said composition in an amount ranging from 0.0001% to 10% by weight relative to the total weight of the composition.

20. A composition according to claim 19, wherein said at least one coupler is present in said composition in an amount ranging from 0.005% to 5% by weight relative to the total weight of the composition.

21. A composition according to claim 16, wherein said acid addition salts are chosen from hydrochlorides, hydrobromides, sulphates, citrates, succinates, tartrates, lactates and acetates.

22. A composition according to claim 18, wherein said acid addition salts are chosen from hydrochlorides, hydrobromides, sulphates, citrates, succinates, tartrates, lactates and acetates.

23. A process for dyeing keratin fibres, comprising applying to said fibres for a sufficient period of time to develop a desired colour at least one dye composition, wherein said at least one dye composition comprises at least one oxidation base, in a medium suitable for dyeing, further wherein said at least one oxidation base is chosen from compounds of formula (I):

acid addition salts thereof, base addition salts thereof, and tautomeric forms thereof:

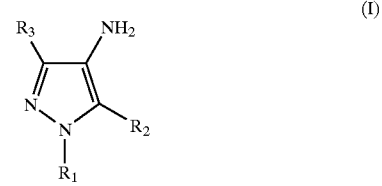

(I)

wherein:

$R_1$ is chosen from hydrogen; Z groups, as defined below; $C_1-C_6$ alkyl radicals; $C_1-C_6$ trifluoroalkyl radicals; $C_1-C_6$ monohydroxyalkyl radicals; $C_2-C_6$ polyhydroxyalkyl radicals; aryl($C_1-C_6$)alkyl radicals; ($C_1-C_6$)alkoxy($C_1-C_6$)alkyl radicals; ($C_1-C_6$) alkylthio($C_1-C_6$)alkyl radicals; amino($C_1-C_6$)

alkylcarbonyl($C_{1-C_6}$)alkyl radicals; N—Z-amino($C_1$–$C_6$)alkylcarbonyl($C_1$–$C_6$)alkyl radicals; N—($C_1$–$C_6$)alkylamino($C_1$–$C_6$)alkylcarbonyl($C_1$–$C_6$)alkyl radicals; N,N-di($C_1$–$C_6$)alkylamino($C_1$–$C_6$)alkylcarbonyl($C_1$–$C_6$)alkyl radicals; $C_1$–$C_6$ aminosulphonylalkyl radicals; $C_1$–$C_6$ N—Z-aminosulphonylalkyl radicals; N—($C_1$–$C_6$)alkylaminosulphonyl($C_1$–$C_6$)alkyl radicals; and N,N-di($C_1$–$C_6$)alkylaminosulphonyl($C_1$–$C_6$)alkyl radicals;

$R_2$ and $R_3$, which may be identical or different, are each chosen from —$NHR_4$ groups; hydroxyl radicals; halogens; nitro radicals; cyano radicals; carboxyl radicals; $C_1$–$C_6$ alkylcarboxyl radicals; carboxyaryl radicals; carbamyl radicals; N—($C_1$–$C_6$)alkylcarbamyl radicals; N,N-di($C_1$–$C_6$)alkylcarbamyl radicals; N-arylcarbamyl radicals; $C_1$–$C_6$ alkoxy radicals; aryloxy radicals; $C_1$–$C_6$ thioalkyl radicals; thioaryl radicals and $R_1$; with the proviso that at least one of $R_2$ and $R_3$ is chosen from —$NHR_4$ groups and a hydroxyl radicals;

$R_4$ is chosen from hydrogen; Z groups as defined below; $C_1$–$C_6$ alkyl radicals; $C_1$–$C_6$ monohydroxyalkyl radicals; $C_2$–$C_6$ polyhydroxyalkyl radicals; ($C_1$–$C_6$)alkoxy($C_1$–$C_6$)alkyl radicals; aryl radicals; benzyl radicals; cyano($C_1$–$C_6$)alkyl radicals; carbamyl($C_1$–$C_6$)alkyl radicals; N—($C_1$–$C_6$)alkylcarbamyl($C_1$–$C_6$)alkyl radicals; N,N-di($C_1$–$C_6$)alkylcarbamyl($C_1$–$C_6$)alkyl radicals; thiocarbamyl($C_1$–$C_6$)alkyl radicals; $C_1$–$C_6$ trifluoroalkyl radicals; $C_1$–$C_6$ sulphoalkyl radicals; ($C_1$–$C_6$)alkylcarboxy($C_1$–$C_6$)alkyl radicals; ($C_1$–$C_6$)alkylsulphinyl($C_1$–$C_6$)alkyl radicals; $C_1$–$C_6$ aminosulphonylalkyl radicals; $C_1$–$C_6$ N—Z-aminosulphonylalkyl radicals; N—($C_1$–$C_6$)alkylaminosulphonyl($C_1$–$C_6$)alkyl radicals; N,N-di($C_1$–$C_6$)alkylaminosulphonyl($C_1$–$C_6$)alkyl radicals; $C_1$–$C_6$ aminoalkyl radicals; $C_1$–$C_6$ aminoalkyl radicals wherein the amine is substituted with one or two radicals, which may be identical or different, chosen from $C_1$–$C_6$ alkyls, $C_1$–$C_6$ monohydroxyalkyls, $C_2$–$C_6$ polyhydroxyalkyls, ($C_1$–$C_6$)alkylcarbonyls, $C_1$–$C_6$ alkylsulphonyls, formyls, trifluoro($C_1$–$C_6$)alkylcarbonyl radicals and Z groups, and further wherein the amine of the $C_1$–$C_6$ aminoalkyl radicals may also be substituted with two radicals forming, together with the nitrogen of said amine, at least one saturated or unsaturated 5- and 6-membered rings which may contain at least one additional hetero atom chosen from nitrogen, oxygen and sulphur;

Z groups, which may be identical or different, are each chosen from groups of formulae (II), (III), and (IV) below:

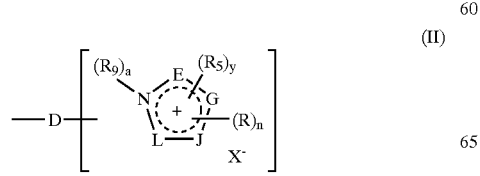
(II)

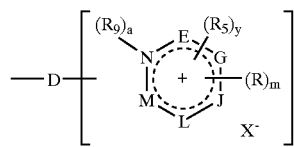
(III)

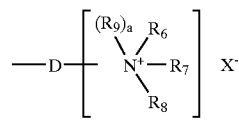
(IV)

wherein:
D is a linker arm chosen from linear and branched divalent alkyl chains wherein said linear and branched alkyl chains can be interrupted by at least one hetero atom and further wherein said linear and branched alkyl divalent chains can be substituted with at least one radical and further wherein said linear and branched divalent alkyl chains can bear at least one ketone function;

the ring members E, G, J, L and M, which may be identical or different, are each chosen from carbon, oxygen, sulphur and nitrogen;

n is an integer ranging from 0 to 4;
m is an integer ranging from 0 to 5;

R, which may be identical or different, are each chosen from Z groups, halogens, hydroxyl radicals, $C_1$–$C_6$ alkyl radicals, $C_1$–$C_6$ monohydroxyalkyl radicals, $C_2$–$C_6$ polyhydroxyalkyl radicals, nitro radicals, cyano radicals, cyano($C_1$–$C_6$)alkyl radicals, $C_1$–$C_6$ alkoxy radicals, tri($C_1$–$C_6$)alkylsilane($C_1$–$C_6$)alkyl radicals, amido radicals, aldehydo radicals, carboxyl radicals, ($C_1$–$C_6$)alkylcarbonyl radicals, thio radicals, $C_1$–$C_6$ thioalkyl radicals, $C_1$–$C_6$ alkylthio radicals, amino radicals, amino radicals protected with at least one radical chosen from ($C_1$–$C_6$) alkylcarbonyl radicals and $C_1$–$C_6$ alkylsulphonyl radicals; NHR" groups and NR"R'" groups wherein R" and R'", which may be identical or different, are each chosen from $C_1$–$C_6$ alkyl radicals, $C_1$–$C_6$ monohydroxyalkyl radicals and $C_2$–$C_6$ polyhydroxyalkyl radicals;

$R_5$ is chosen from $C_1$–$C_6$ alkyl radicals, $C_1$–$C_6$ monohydroxyalkyl radicals, $C_2$–$C_6$ polyhydroxyalkyl radicals, cyano($C_1$–$C_6$)alkyl radicals, tri($C_1$–$C_6$)alkylsilane($C_1$–$C_6$)alkyl radicals, ($C_1$–$C_6$)alkoxy($C_1$–$C_6$)alkyl radicals, carbamyl($C_1$–$C_6$)alkyl radicals, ($C_1$–$C_6$)alkylcarboxy($C_1$–$C_6$)alkyl radicals, benzyl radicals and Z groups.

$R_6$, $R_7$ and $R_8$, which may be identical or different, are each chosen from $C_1$–$C_6$ alkyl radicals, $C_1$–$C_6$ monohydroxyalkyl radicals, $C_2$–$C_6$ polyhydroxyalkyl radicals, ($C_1$–$C_6$)alkoxy($C_1$–$C_6$)alkyl radicals, cyano($C_1$–$C_6$)alkyl radicals, aryl radicals, benzyl radicals, $C_1$–$C_6$ amidoalkyl radicals, tri($C_1$–$C_6$)alkylsilane($C_1$–$C_6$)alkyl radicals and $C_1$–$C_6$ aminoalkyl radicals wherein the amine is protected with at least one radical chosen from ($C_1$–$C_6$)alkylcarbonyl radicals and $C_1$–$C_6$ alkylsulphonyl radicals;

at least two of the radicals $R_6$, $R_7$ and $R_8$ can together also form, with the nitrogen to which they are attached, at least one saturated ring chosen from saturated 5- and 6-membered rings and rings comprising at least one additional hetero atom, wherein said at least one saturated ring is optionally substituted with at least one entity chosen from halogens, hydroxyl radicals, $C_1$–$C_6$ alkyl radicals, $C_1$–$C_6$ monohydroxyalkyl radicals, $C_2$–$C_6$ polyhydroxyalkyl radicals, nitro radicals, cyano radicals, cyano($C_1$–$C_6$)alkyl radicals, $C_1$–$C_6$ alkoxy radicals, tri($C_1$–$C_6$)alkylsilane ($C_1$–$C_6$)alkyl radicals, amido radicals, aldehydo radicals, carboxyl radicals, keto($C_1$–$C_6$)alkyl radicals, thio radicals, $C_1$–$C_6$ thioalkyl radicals, $C_1$–$C_6$ alkylthio radicals, amino radicals, and amino radicals protected with at least one radical chosen from ($C_1$–$C_6$)alkylcarbonyls and $C_1$–$C_6$ alkylsulphonyl radicals; with the proviso that one of $R_6$, $R_7$, and $R_8$ may also be chosen from Z groups.

$R_9$ is chosen from $C_1$–$C_6$ alkyl radicals; $C_1$–$C_6$ monohydroxyalkyl radicals; $C_2$–$C_6$ polyhydroxyalkyl radicals; aryl radicals; benzyl radicals; $C_1$–$C_6$ aminoalkyl, $C_1$–$C_6$ aminoalkyl radicals wherein the amine is protected with at least one radical chosen from ($C_1$–$C_6$) alkylcarbonyl radicals and $C_1$–$C_6$ alkylsulphonyl radicals; carboxy($C_1$–$C_6$)alkyl radicals; cyano ($C_1$–$C_6$)alkyl radicals; carbamyl($C_1$–$C_6$)alkyl radicals; $C_1$–$C_6$ trifluoroalkyl radicals; tri($C_1$–$C_6$) alkylsilane($C_1$–$C_6$)alkyl radicals; $C_1$–$C_6$ sulphonamidoalkyl radicals; ($C_1$–$C_6$)alkylcarboxy ($C_1$–$C_6$)alkyl radicals; ($C_1$–$C_6$)alkylsulphinyl ($C_1$–$C_6$)alkyl radicals; ($C_1$–$C_6$)alkylsulphonyl ($C_{C6}$)alkyl radicals; ($C_1$–$C_6$)alkylketo($C_1$–$C_6$) alkyl radicals; N—($C_1$–$C_6$)alkylcarbamyl($C_1$–$C_6$) alkyl radicals; and N—($C_1$–$C_6$) alkylsulphonamido($C_1$–$C_6$)alkyl radicals;

a and y are integers equal to 0 or 1;
with the proviso that in the unsaturated cationic groups of formula (II):
when a=0, the linker arm D is attached to a nitrogen, with the proviso that said nitrogen is not chosen from E, G, J, and L.
when a=1, the linker arm D is attached to one of the ring members chosen from E, G, J and L, and y=1 when:
1) the ring members E, G, J and L are simultaneously chosen from carbons and the radical $R_5$ is borne by the nitrogen of the unsaturated ring of said groups of formula (II) and a=0; or
2) at least one of the ring members E, G, J and L is chosen from nitrogen and said radical $R_5$ is attached to said at least one ring member;

the proviso that in the unsaturated cationic groups of formula (III):
when a=0, the linker arm D is attached to the nitrogen, with the proviso that said nitrogen is not chosen from E, G, J, and L.
when a=1, the linker arm D is attached to one of the ring members E, G, J, L or M,
y=1 when at least one of the ring members E, G, J, L and M is chosen from divalent atoms and when the radical $R_5$ is borne by the nitrogen of the unsaturated ring of formula (III);

with the proviso that in the cationic groups of formula (IV):
when a=0, then the linker arm is attached to the nitrogen bearing the radicals $R_6$, $R_7$, and $R_8$,
when a=1, then two of the radicals chosen from $R_6$, $R_7$, and $R_8$ form, together with the nitrogen to which they are attached, at least one ring chosen from 5- and 6-membered saturated rings as defined above, and the linker arm D is borne by a carbon of said saturated ring;

$X^-$ is chosen from monovalent anions and divalent anions;

with the proviso that said compound of formula (I), acid additional salt, base addition salt, or tautomeric form comprises at least one Z group.

24. A process according to claim 23, wherein said keratin fibres are chosen from hair.

25. A process according to claim 23 wherein said desired color is developed at acidic or alkaline pH.

26. A process according to claim 23, wherein said dye composition further comprises at least one oxidizing agent.

27. A process according to claim 26, wherein said at least one oxidizing agent is added to said dye composition at the time of use.

28. A process according to claim 23, further comprising applying at least one oxidizing composition to said keratin fibres.

29. A process according to claim 28, wherein said at least one oxidizing composition comprises at least one oxidizing agent.

30. A process according to claim 23, wherein said at least one oxidizing composition is applied simultaneously with said at least one dye composition.

31. A process according to claim 26, wherein said at least one oxidizing agent is chosen from hydrogen peroxide, urea peroxide, alkali metal bromates, persalts, and enzymes.

32. A process according to claim 31, wherein said persalts are chosen from perborates and persulphates.

33. A process according to claim 29, wherein said at least one oxidizing agent is chosen from hydrogen peroxide, urea peroxide, alkali metal bromates, persalts, and enzymes.

34. A process according to claim 33, wherein said persalts are chosen from perborates and persulphates.

35. A process according to claim 23, wherein said at least one oxidizing composition is applied sequentially with said at least one dye composition.

36. A multi-compartment "kit" comprising a first compartment comprising at least one dye composition, wherein said at least one dye composition comprises at least one oxidation base, further wherein said at least one oxidation base is chosen from compounds of formula (I):
acid addition salts thereof, base addition salts thereof, and tautomeric forms thereof:

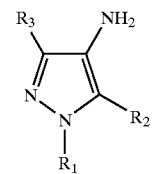

(I)

wherein:
$R_1$ is chosen from hydrogen; Z groups, as defined below; $C_1$–$C_6$ alkyl radicals; $C_1$–$C_6$ trifluoroalkyl radicals; $C_1$–$C_6$ monohydroxyalkyl radicals; $C_2$–$C_6$ polyhydroxyalkyl radicals; aryl($C_1$–$C_6$)alkyl radicals; ($C_1$–$C_6$)alkoxy($C_1$–$C_6$)alkyl radicals; ($C_1$–$C_6$) alkylthio($C_1$–$C_6$)alkyl radicals; amino($C_1$–$C_6$) alkylcarbonyl($C_1$–$C_6$)alkyl radicals; N—Z-amino ($C_1$–$C_6$)alkylcarbonyl($C_1$–$C_6$)alkyl radicals; N—($C_1$–$C_6$)alkylamino($C_1$–$C_6$)alkylcarbonyl ($C_1$–$C_6$)alkyl radicals; N,N-di($C_1$–$C_6$)alkylamino($C_1$–$C_6$)alkylcarbonyl($C_1$–$C_6$)alkyl radicals; $C_1$–$C_6$ aminosulphonylalkyl radicals; $C_1$–$C_6$ N—Z-aminosulphonylalkyl radicals; N—($C_1$–$C_6$)alkylaminosulphonyl($C_1$–$C_6$)alkyl radicals; and N,N-di($C_1$–$C_6$)alkylaminosulphonyl($C_1$–$C_6$)alkyl radicals;

$R_2$ and $R_3$, which may be identical or different, are each chosen from —$NHR_4$ groups; hydroxyl radicals; halogens; nitro radicals; cyano radicals; carboxyl radicals; $C_1$–$C_6$ alkylcarboxyl radicals; carboxyaryl radicals; carbamyl radicals; N—($C_1$–$C_6$)alkylcarbamyl radicals; N,N-di($C_1$–$C_6$)alkylcarbamyl radicals; N-arylcarbamyl radicals; $C_1$–$C_6$ alkoxy radicals; aryloxy radicals; $C_1$–$C_6$ thioalkyl radicals; thioaryl radicals and $R_1$; with the proviso that at least one of $R_2$ and $R_3$ is chosen from —$NHR_4$ groups and a hydroxyl radicals;

$R_4$ is chosen from hydrogen; Z groups as defined below; $C_1$–$C_6$ alkyl radicals; $C_1$–$C_6$ monohydroxyalkyl radicals; $C_2$–$C_6$ polyhydroxyalkyl radicals; ($C_1$–$C_6$)alkoxy($C_1$–$C_6$)alkyl radicals; aryl radicals; benzyl radicals; cyano($C_1$–$C_6$)alkyl radicals; carbamyl($C_1$–$C_6$)alkyl radicals; N—($C_1$–$C_6$)alkylcarbamyl($C_1$–$C_6$)alkyl radicals; N,N-di($C_1$–$C_6$)alkylcarbamyl($C_1$–$C_6$)alkyl radicals; thiocarbamyl($C_1$–$C_6$)alkyl radicals; $C_1$–$C_6$ trifluoroalkyl radicals; $C_1$–$C_6$ sulphoalkyl radicals; ($C_1$–$C_6$)alkylcarboxy($C_1$–$C_6$)alkyl radicals; ($C_1$–$C_6$)alkylsulphinyl($C_1$–$C_6$)alkyl radicals; $C_1$–$C_6$ aminosulphonylalkyl radicals; $C_1$–$C_6$ N—Z-aminosulphonylalkyl radicals; N—($C_1$–$C_6$)alkylaminosulphonyl($C_1$–$C_6$)alkyl radicals; N,N-di($C_1$–$C_6$)alkylaminosulphonyl($C_1$–$C_6$)alkyl radicals; $C_1$–$C_6$ aminoalkyl radicals; $C_1$–$C_6$ aminoalkyl radicals wherein the amine is substituted with one or two radicals, which may be identical or different, chosen from $C_1$–$C_6$ alkyls, $C_1$–$C_6$ monohydroxyalkyls, $C_2$–$C_6$ polyhydroxyalkyls, ($C_1$–$C_6$)alkylcarbonyls, $C_1$–$C_6$ alkylsulphonyls, formyls, trifluoro($C_1$–$C_6$)alkylcarbonyl radicals and Z groups, and further wherein the amine of the $C_1$–$C_6$ aminoalkyl radicals may also be substituted with two radicals forming, together with the nitrogen of said amine, at least one saturated or unsaturated 5- and 6-membered rings which may contain at least one additional hetero atom chosen from nitrogen, oxygen and sulphur;

Z groups, which may be identical or different, are each chosen from groups of formulae (II), (III), and (IV) below:

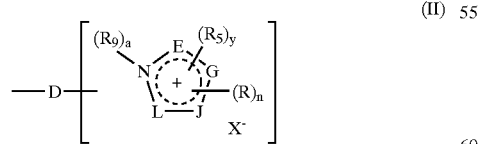
(II)

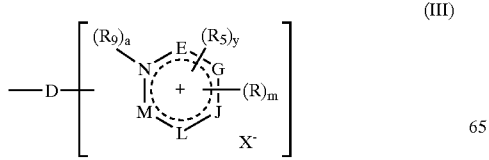
(III)

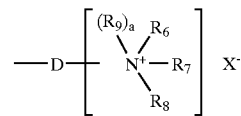
(IV)

wherein:

D is a linker arm chosen from linear and branched divalent alkyl chains wherein said linear and branched alkyl chains can be interrupted by at least one hetero atom and further wherein said linear and branched alkyl divalent chains can be substituted with at least one radical and further wherein said linear and branched divalent alkyl chains can bear at least one ketone function;

the ring members E, G, J, L and M, which may be identical or different, are each chosen from carbon, oxygen, sulphur and nitrogen;

n is an integer ranging from 0 to 4;

m is an integer ranging from 0 to 5;

R, which may be identical or different, are each chosen from Z groups, halogens, hydroxyl radicals, $C_1$–$C_6$ alkyl radicals, $C_1$–$C_6$ monohydroxyalkyl radicals, $C_2$–$C_6$ polyhydroxyalkyl radicals, nitro radicals, cyano radicals, cyano($C_1$–$C_6$)alkyl radicals, $C_1$–$C_6$ alkoxy radicals, tri($C_1$–$C_6$)alkylsilane($C_1$–$C_6$)alkyl radicals, amido radicals, aldehydo radicals, carboxyl radicals, ($C_1$–$C_6$)alkylcarbonyl radicals, thio radicals, $C_{1-C6}$ thioalkyl radicals, $C_1$–$C_6$ alkylthio radicals, amino radicals, amino radicals protected with at least one radical chosen from ($C_1$–$C_6$) alkylcarbonyl radicals and $C_1$–$C_6$ alkylsulphonyl radicals; NHR" groups and NR"R'" groups wherein R" and R'", which may be identical or different, are each chosen from $C_1$–$C_6$ alkyl radicals, $C_1$–$C_6$ monohydroxyalkyl radicals and $C_2$–$C_6$ polyhydroxyalkyl radicals;

$R_5$ is chosen from $C_1$–$C_6$ alkyl radicals, $C_1$–$C_6$ monohydroxyalkyl radicals, $C_2$–$C_6$ polyhydroxyalkyl radicals, cyano($C_1$–$C_6$)alkyl radicals, tri($C_1$–$C_6$)alkylsilane($C_1$–$C_6$)alkyl radicals, ($C_1$–$C_6$)alkoxy($C_1C_6$)alkyl radicals, carbamyl($C_1$–$C_6$)alkyl radicals, ($C_1$–$C_6$)alkylcarboxy($C_1$–$C_6$)alkyl radicals, benzyl radicals and Z groups.

$R_6$, $R_7$ and $R_8$, which may be identical or different, are each chosen from $C_1$–$C_6$ alkyl radicals, $C_1$–$C_6$ monohydroxyalkyl radicals, $C_2$–$C_6$ polyhydroxyalkyl radicals, ($C_1$–$C_6$)alkoxy($C_1$–$C_6$)alkyl radicals, cyano($C_1$–$C_6$)alkyl radicals, aryl radicals, benzyl radicals, $C_1$–$C_6$ amidoalkyl radicals, tri($C_1$–$C_6$)alkylsilane($C_1$–$C_6$)alkyl radicals and $C_1$–$C_6$ aminoalkyl radicals wherein the amine is protected with at least one radical chosen from ($C_1$–$C_6$)alkylcarbonyl radicals and $C_1$–$C_6$ alkylsulphonyl radicals;

at least two of the radicals $R_6$, $R_7$ and $R_8$ can together also form, with the nitrogen to which they are attached, at least one saturated ring chosen from saturated 5- and 6-membered rings and rings comprising at least one additional hetero atom, wherein said at least one saturated ring is optionally substituted with at least one entity chosen from halogens, hydroxyl radicals, $C_1$–$C_6$ alkyl radicals, $C_1$–$C_6$ monohydroxyalkyl radicals, $C_2$–$C_6$ polyhydroxyalkyl radicals, nitro radicals, cyano radicals, cyano($C_1$–$C_6$)alkyl radicals, $C_1$–$C_6$ alkoxy radicals, tri($C_1$–$C_6$)alkylsilane ($C_1$–$C_6$)alkyl radicals, amido radicals, aldehydo radicals, carboxyl radicals, keto($C_1$–$C_6$)alkyl radicals, thio radicals, $C_1$–$C_6$ thioalkyl radicals, $C_1$–$C_6$ alkylthio radicals, amino radicals, and amino radicals protected with at least one radical chosen from ($C_1$–$C_6$)alkylcarbonyls and $C_1$–$C_6$ alkylsulphonyl radicals; with the proviso that one of $R_6$, $R_7$, and $R_8$ may also be chosen from Z groups.

$R_9$ is chosen from $C_1$–$C_6$ alkyl radicals; $C_1$–$C_6$ monohydroxyalkyl radicals; $C_2$–$C_6$ polyhydroxyalkyl radicals; aryl radicals; benzyl radicals; $C_1$–$C_6$ aminoalkyl radicals, $C_1$–$C_6$ aminoalkyl radicals wherein the amine is protected with at least one radical chosen from ($C_1$–$C_6$) alkylcarbonyl radicals and $C_1$–$C_6$ alkylsulphonyl radicals; carboxy($C_1$–$C_6$)alkyl radicals; cyano ($C_1$–$C_6$)alkyl radicals; carbamyl($C_1$–$C_6$)alkyl radicals; $C_1$–$C_6$ trifluoroalkyl radicals; tri($C_1$–$C_6$) alkylsilane($C_1$–$C_6$)alkyl radicals; $C_1$–$C_6$ sulphonamidoalkyl radicals; ($C_1$–$C_6$)alkylcarboxy ($C_1$–$C_6$)alkyl radicals; ($C_1$–$C_6$)alkylsulphinyl ($C_1$–$C_6$)alkyl radicals; ($C_1$–$C_6$)alkylsulphonyl ($C_1$–$C_6$)alkyl radicals; ($C_1$–$C_6$)alkylketo($C_1$–$C_6$) alkyl radicals; N—($C_1$–$C_6$)alkylcarbamyl($C_1$–$C_6$) alkyl radicals; and N—($C_1$–$C_6$) alkylsulphonamido($C_1$–$C_6$)alkyl radicals;

a and y are integers equal to 0 or 1;
  with the proviso that in the unsaturated cationic groups of formula (II):
  when a=0, the linker arm D is attached to a nitrogen, with the proviso that said nitrogen is not chosen from E, G, J, and L.
  when a=1, the linker arm D is attached to one of the ring members chosen from E, G, J and L, and y=1 when:

1) the ring members E, G, J and L are simultaneously chosen from carbons and the radical $R_5$ is borne by the nitrogen of the unsaturated ring of said groups of formula (II) and a=0; or
2) at least one of the ring members E, G, J and L is chosen from nitrogen and said radical $R_5$ is attached to said at least one ring member;

with the proviso that in the unsaturated cationic groups of formula (III):
  when a=0, the linker arm D is attached to the nitrogen, with the proviso that said nitrogen is not chosen from E, G, J, and L.
  when a=1, the linker arm D is attached to one of the ring members E, G, J, L or M,
  y=1 when at least one of the ring members E, G, J, L and M is chosen from divalent atoms and when the radical $R_5$ is borne by the nitrogen of the unsaturated ring of formula (III);

with the proviso that in the cationic groups of formula (IV):
  when a=0, then the linker arm is attached to the nitrogen bearing the radicals $R_6$, $R_7$, and $R_8$,
  when a=1, then two of the radicals chosen from $R_6$, $R_7$, and $R_8$ form, together with the nitrogen to which they are attached, at least one ring chosen from 5- and 6-membered saturated rings as defined above, and the linker arm D is borne by a carbon of said saturated ring;

$X^-$ is chosen from monovalent anions and divalent anions;

with the proviso that said compound of formula (I), acid additional salt, base addition salt, or tautomeric form comprises at least one Z group, and a second compartment comprising at least one oxidizing composition.

\* \* \* \* \*

UNITED STATES PATENT AND TRADEMARK OFFICE
CERTIFICATE OF CORRECTION

PATENT NO.    : 6,660,046 B1  
DATED         : December 9, 2003  
INVENTOR(S)   : Terranova et al.

It is certified that error appears in the above-identified patent and that said Letters Patent is hereby corrected as shown below:

Title page,
Item [54], Title, "OF DYEING" should read -- FOR DYEING --.
Item [75], Inventors, "Bois Colombes" should read -- Magagnosc --.

Column 16,
Lines 25-26, "N-$(C_1-C_6)$alkylamino$(C_1C_6)$alkylcarbonyl$(C_1-C_6)$alkyl" should read -- N-$(C_1-C_6)$alkylamino$(C_1-C_6)$alkylcarbonyl$(C_1-C_6)$alkyl --.
Line 43, "a hydroxyl radicals;" should read -- a hydroxyl radical --.

Column 18,
Line 13, "5- and an 6-membered" should read -- 5- and 6-membered --.

Column 19,
Line 20, "additional salt," should read -- addition salt, --.
Line 35, "claims 1," should read -- claim 1, --.
Line 62, "pyrimidin" should read -- pyrimidine --.

Column 20, line 67 to Column 21, line 1,
"amino $(C_1-C_6)$alkylcarbonyl$(C_{1-C6})$alkyl" should read -- amino$(C_1-C_6)$alkylcarbonyl$(C_1-C_6)$alkyl --.

Column 21,
Line 23, "a hydroxyl radicals;" should read -- a hydroxyl radical; --.

Column 23,
Lines 30-31, "$(C_1-C_6)$alkylsulphonyl$(C_{C6})$alkyl" should read -- $(C_1-C_6)$alkylsulphonyl$(C_1-C_6)$alkyl --.
Line 51, before "the proviso" insert -- with --.

Column 24,
Line 8, "additional salt," should read -- addition salt --.

UNITED STATES PATENT AND TRADEMARK OFFICE
CERTIFICATE OF CORRECTION

PATENT NO. : 6,660,046 B1
DATED : December 9, 2003
INVENTOR(S) : Terranova et al.

It is certified that error appears in the above-identified patent and that said Letters Patent is hereby corrected as shown below:

Column 25,
Line 19, "a hydroxyl radicals;" should read -- a hydroxyl radical; --.

Column 26,
Line 31, "$C_1$-$_{C_6}$ thioalkyl" should read -- $C_1$-$C_6$ thioalkyl --.
Lines 43-44, "($C_1$-$C_6$)alkoxy($C_1C_6$)alkyl" should read -- ($C_1$-$C_6$)alkoxy($C_1$-$C_6$)alkyl --.

Column 28,
Line 33, "additional salt," should read -- addition salt, --.

Signed and Sealed this

Eighth Day of June, 2004

JON W. DUDAS
*Acting Director of the United States Patent and Trademark Office*